(12) United States Patent
Elliott

(10) Patent No.: US 7,349,194 B2
(45) Date of Patent: Mar. 25, 2008

(54) METHOD AND SYSTEM FOR ELECTRICALLY CONNECTING THE HUMAN (AND VERTEBRATE) ORGANISM TO EARTH SO AS TO FACILITATE A CURRENT FLOW BETWEEN THE HUMAN BIOPOTENTIAL AND EARTH FOR THE PURPOSE OF PROMOTING HEALTH, WELL BEING, AND PERFORMANCE

(75) Inventor: Stephen Bennett Elliott, Allen, TX (US)

(73) Assignee: Coherence LLC, Allen, TX (US)

( * ) Notice: Subject to any disclaimer, the term of this patent is extended or adjusted under 35 U.S.C. 154(b) by 350 days.

(21) Appl. No.: 11/187,144

(22) Filed: Jul. 22, 2005

(65) Prior Publication Data

US 2007/0019359 A1   Jan. 25, 2007

(51) Int. Cl.
*H01H 47/00* (2006.01)
(52) U.S. Cl. ..................... 361/220; 361/232
(58) Field of Classification Search ............... 361/220, 361/232
See application file for complete search history.

(56) References Cited

U.S. PATENT DOCUMENTS

| | | | | |
|---|---|---|---|---|
| 4,557,271 A | * | 12/1985 | Stoller et al. | 600/547 |
| 4,800,374 A | * | 1/1989 | Jacobson | 340/649 |
| 5,448,840 A | * | 9/1995 | Cheskin | 36/32 R |
| 6,683,779 B2 | | 1/2004 | Ober | |

* cited by examiner

Primary Examiner—Stephen W. Jackson
(74) Attorney, Agent, or Firm—Withrow & Terranova, PLLC

(57) ABSTRACT

The present invention specifies the fundamental method and system for providing an electrical connection between the human and earth ground for purposes of promoting health, well being, and performance. It is based on the premise that vertebrate organisms require electrical connectivity to earth for health and well being, especially during times of trauma. It is asserted that vertebrate biopotential may be modulated by varying the resistance from the body to earth ground and that via this mechanism, bioenergy production and internal impedance may be modulated for purposes of healing, health maintenance, and "work" including exercise. Instructive methods for characterizing an individual's biopotential and for applying the present invention in urgent portable medical care situations are provided.

25 Claims, 9 Drawing Sheets

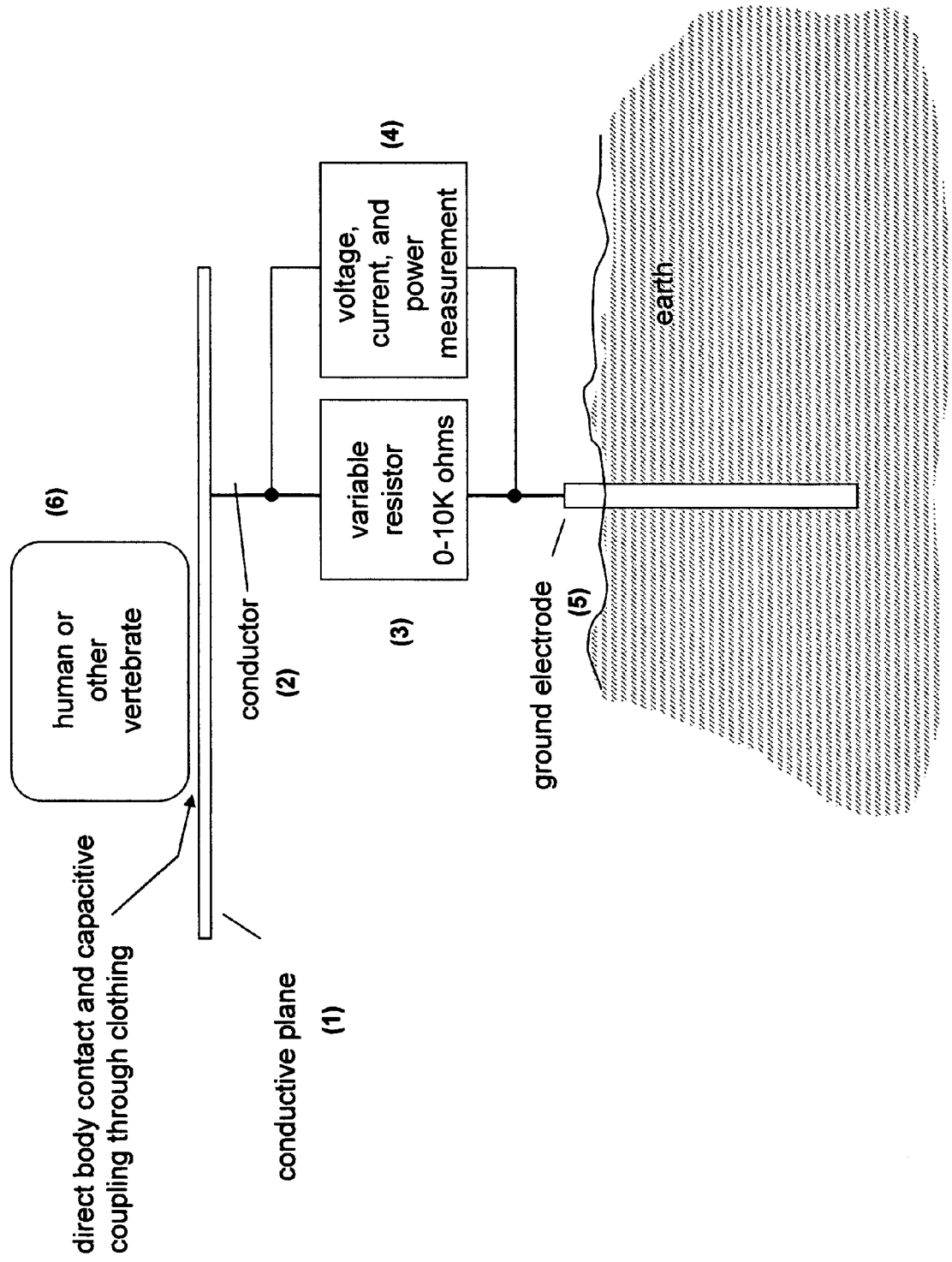

| R Value | Voltage | Current | Power | Body Z |
|---|---|---|---|---|
| open voltage | 0.01944504 | NA | NA | NA |
| 0 | 0.00000000 | to be measured | to be measured | to be measured |
| 4.96 | 0.00000124 | 0.00000025 | 0.00000000 | 77704 |
| 7.5 | 0.00007100 | 0.00000947 | 0.00000000 | 2047 |
| 9.9 | 0.00029908 | 0.00003021 | 0.00000001 | 634 |
| 19.81 | 0.00115769 | 0.00005844 | 0.00000007 | 313 |
| 29.69 | 0.00188650 | 0.00006354 | 0.00000012 | 276 |
| 39.56 | 0.00277943 | 0.00007026 | 0.00000020 | 237 |
| 46.39 | 0.00324054 | 0.00006985 | 0.00000023 | 232 |
| 56.2 | 0.00380661 | 0.00006773 | 0.00000026 | 231 |
| 66.1 | 0.00453736 | 0.00006864 | 0.00000031 | 217 |
| 76 | 0.00522036 | 0.00006869 | 0.00000036 | 207 |
| 85.8 | 0.00585945 | 0.00006829 | 0.00000040 | 199 |
| 98.1 | 0.00678035 | 0.00006912 | 0.00000047 | 183 |
| 146.5 | 0.00893804 | 0.00006101 | 0.00000055 | 172 |
| 266 | 0.01253182 | 0.00004711 | 0.00000059 | 147 |
| 461 | 0.01745105 | 0.00003785 | 0.00000066 | 53 |
| 552 | 0.01478850 | 0.00002679 | 0.00000040 | 174 |
| 669 | 0.01516013 | 0.00002266 | 0.00000034 | 189 |
| 985 | 0.01447633 | 0.00001470 | 0.00000021 | 338 |
| 1471 | 0.01266294 | 0.00000861 | 0.00000011 | 788 |
| 2163 | 0.01076207 | 0.00000498 | 0.00000005 | 1745 |
| 3234 | 0.01093867 | 0.00000338 | 0.00000004 | 2515 |
| 3810 | 0.01117355 | 0.00000293 | 0.00000003 | 2820 |
| 4598 | 0.00957919 | 0.00000208 | 0.00000002 | 4736 |
| 9850 | 0.01117004 | 0.00000113 | 0.00000001 | 7297 |
| 98354 | 0.01056433 | 0.00000011 | 0.00000000 | 82679 |
| 984020 | 0.01604641 | 0.00000002 | 0.00000000 | 208416 |

Figure B

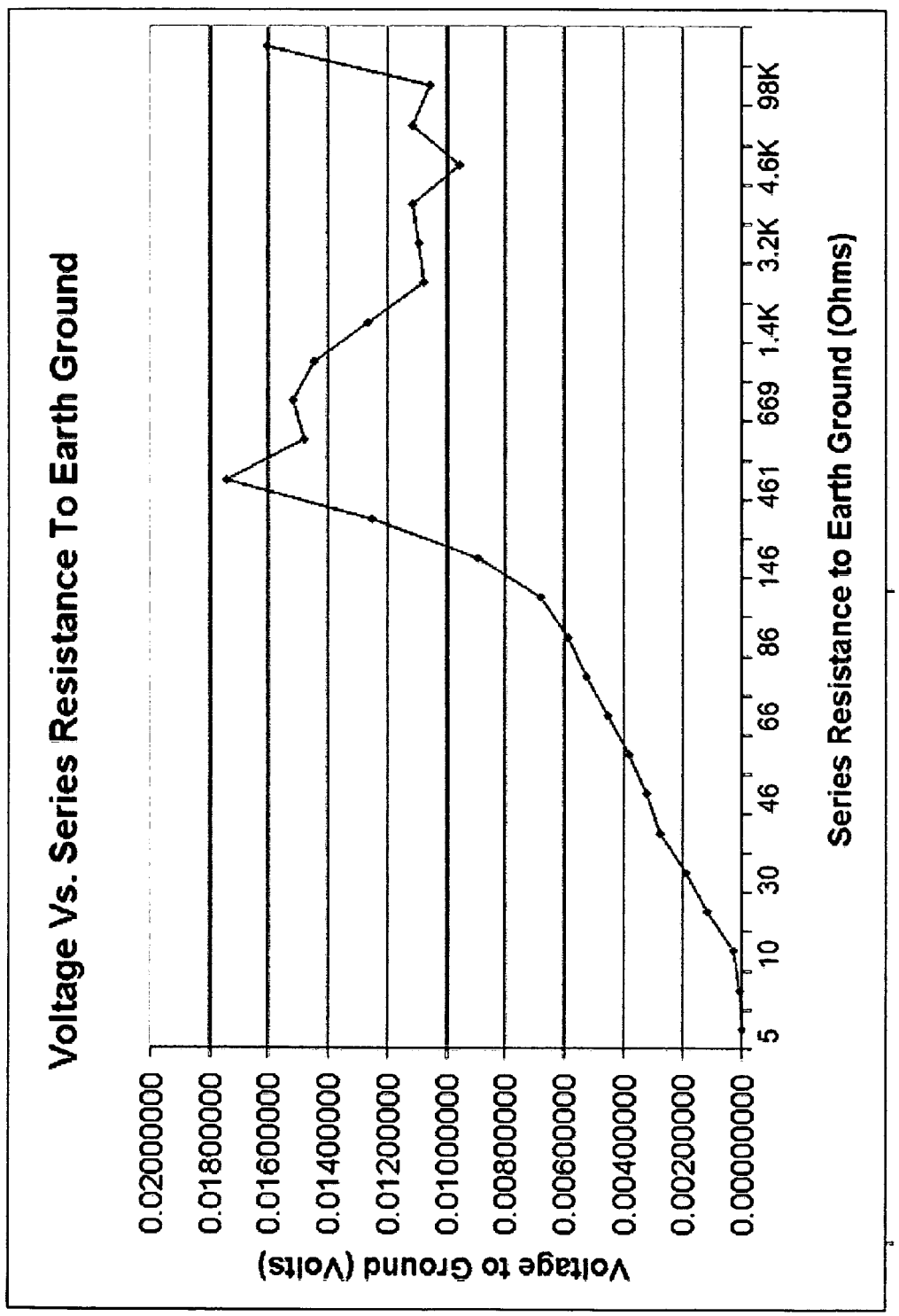
Figure C

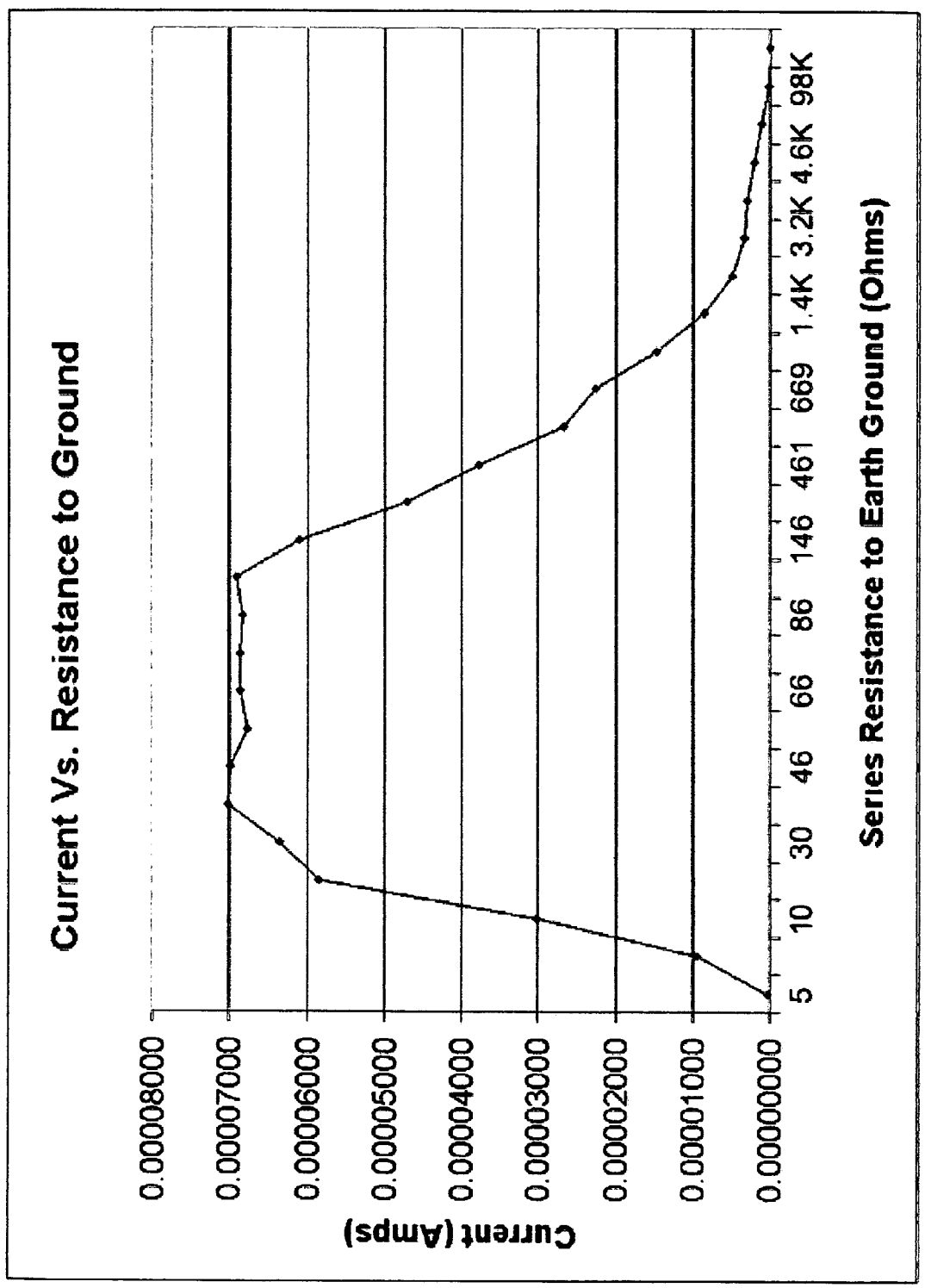
Figure D

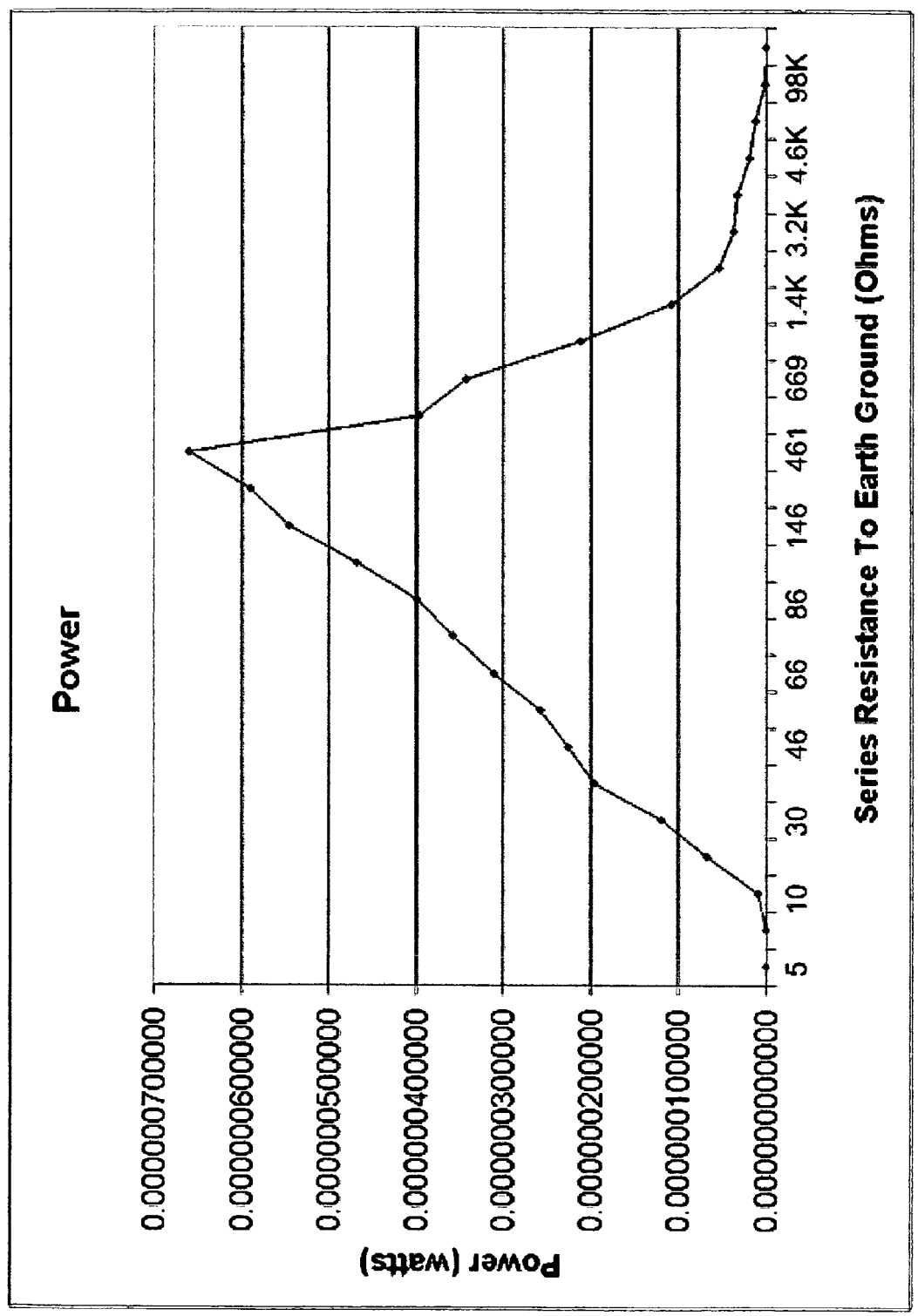
Figure E

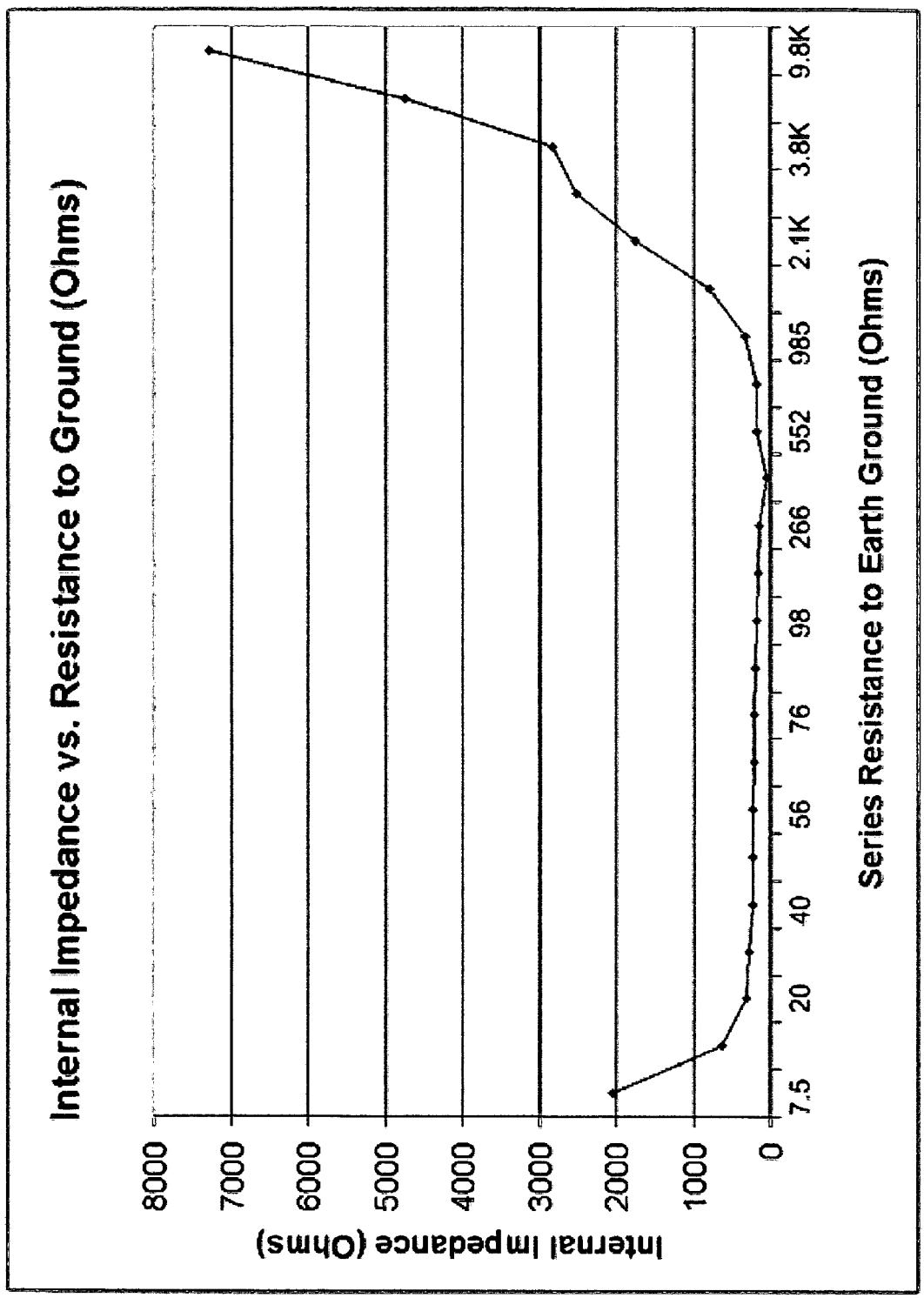
Figure F

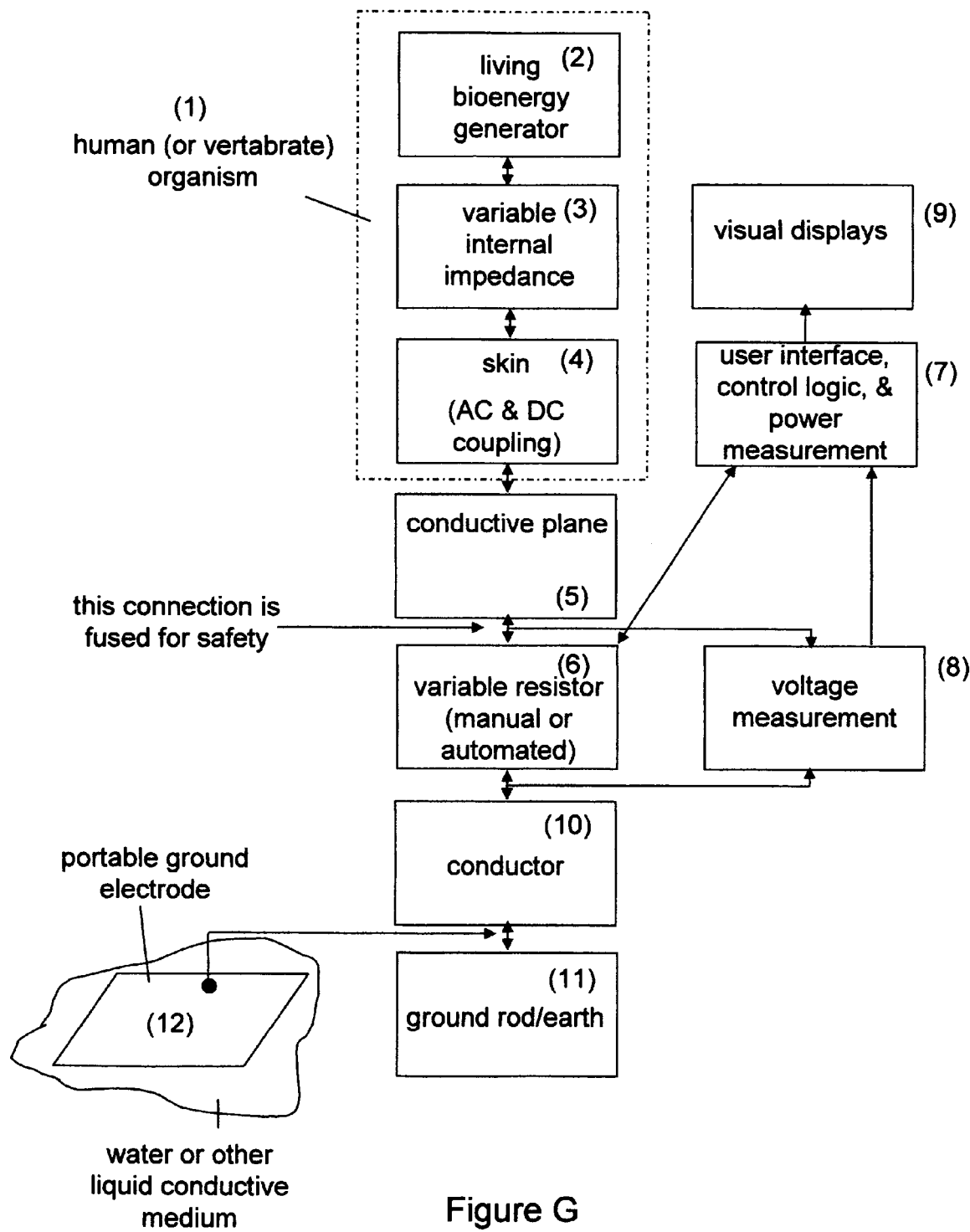
Figure G

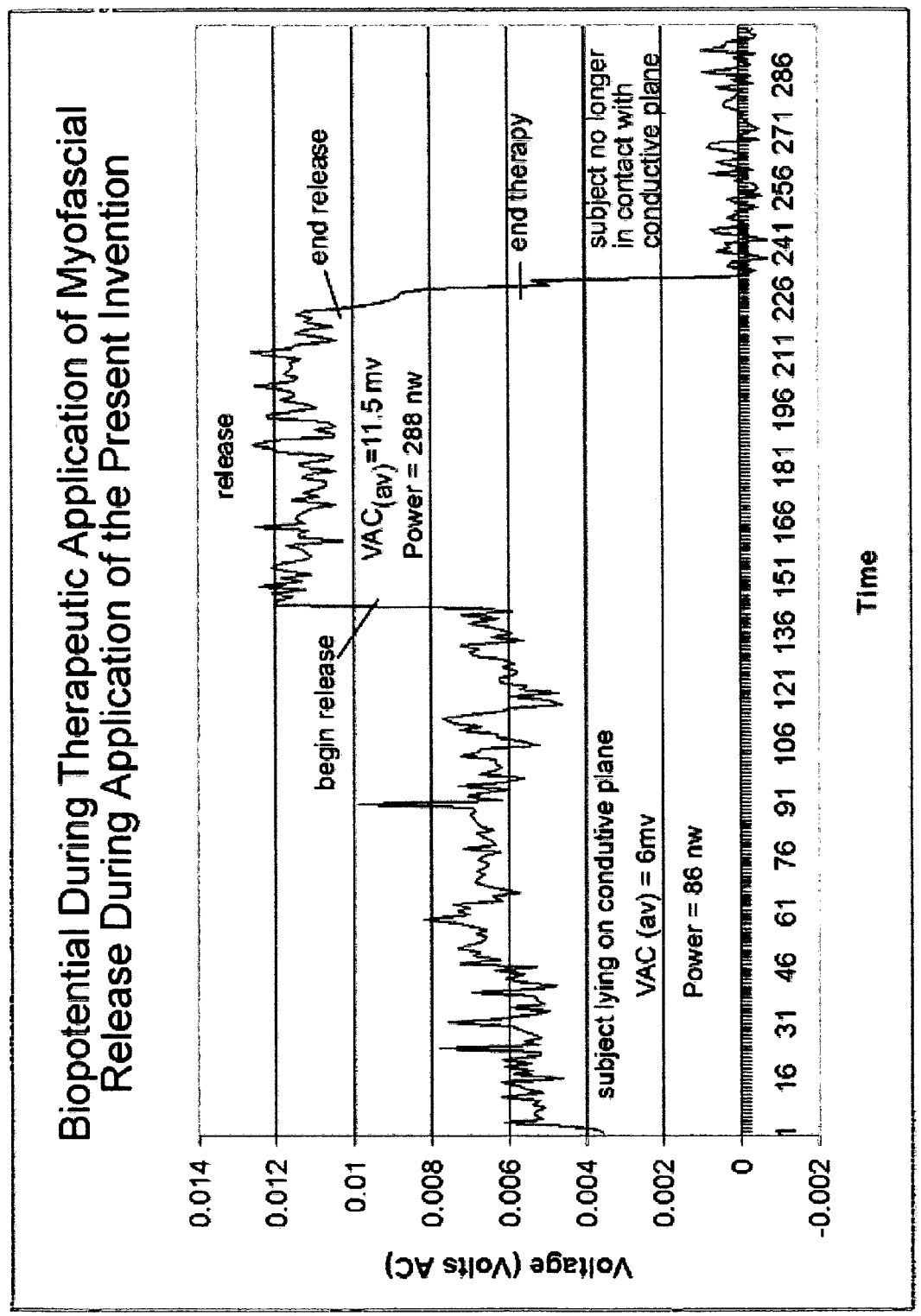
Figure H

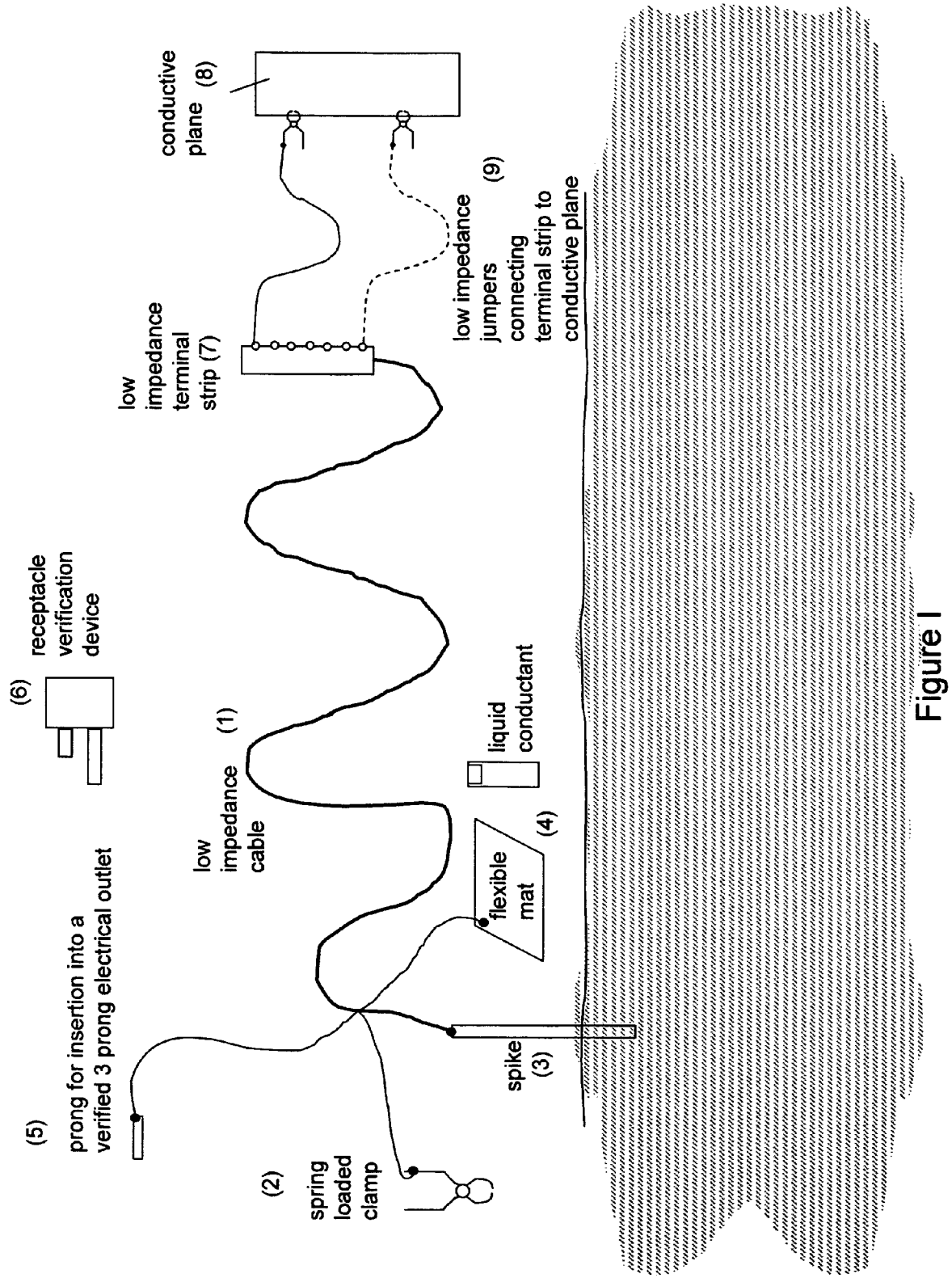
Figure I

METHOD AND SYSTEM FOR ELECTRICALLY CONNECTING THE HUMAN (AND VERTEBRATE) ORGANISM TO EARTH SO AS TO FACILITATE A CURRENT FLOW BETWEEN THE HUMAN BIOPOTENTIAL AND EARTH FOR THE PURPOSE OF PROMOTING HEALTH, WELL BEING, AND PERFORMANCE

FIELD OF THE INVENTION

The present invention relates to the field of vertebrate health and performance and in particular to the field of the human bioenergy system and the electrical relationship of that system to earth.

BACKGROUND OF THE INVENTION

All terrestrial organisms have an electrical relationship with earth. In their native environments, all flora and fauna are in electrical contact with earth, either directly, as in standing or lying on the ground, immersed in water, or indirectly, as in perched above ground in a plant, a simple example being an arbor dwelling bird.

More specifically, the human organism shares this relationship with all other vertebrate life, that is, vertebrate life forms possess a similar bioenergetic response and requirement for electrical contact with earth.

Via civilization, humans in particular have lost what was once a natural connectedness with earth by adopting insulating clothing and habitat. This is to say that the typical civilized man no longer walks barefoot and no longer sits or sleeps on the ground. Floors, furniture, beds, clothing, and in particular, shoes, are typically highly insulating, cutting off an effective electrical connection between human and ground. Domesticated home dwelling animals often share this condition.

This patent application presents research that demonstrates that the human organism desires a certain electrical connectedness with earth and strives to maintain it. A like function has been confirmed to exist with the canine species. This author also asserts that while subtle, this connection is essential to optimal health, well being, and performance. The lack of this connection has a negative impact on all aspects of life, physical, mental, and spiritual, during both waking and sleeping hours. This author asserts that the lack of this connection is a key factor affecting the tendency toward chaos or "incoherence" of human biosystems, specific examples being incoherent variability of the heart rhythm as evidenced by the electrocardiogram, as well as incoherent brain function as evidenced by the electroencephalogram. This tendency toward incoherence is evidenced in most of today's modern civilized societies. This, as opposed to "coherence" which this author asserts is reinforced via "grounding" by "sinking" spurious high energy currents that are both generated by the vertebrate biosystem as well as coupled thereto from insulated high energy devices, an example being a cathode ray tube.

Interestingly, the bioenergetic system of the vertebrate organism responds dramatically to relatively small changes in the impedance between itself and earth ground, ramping up or ramping down energy production and internal impedance as a function of connectedness. FIGS. B, C, D, E, and F characterize the typical human response to variations in resistance between body and ground. Figure B presents a table depicting these changes in resistance-to-ground and corresponding changes in "bio" voltage, current, power, and internal impedance. This is measured employing the system of the present invention as depicted in FIG. A.

It has been determined that it is particularly important that the human (vertebrate) body be grounded during times of high stress or trauma. This is because biopotential increases dramatically during these times. Humans are the only animals known to suffer from post traumatic stress. A key reason for this is that all other animals suffer stress while electrically connected to earth and bioenergies of trauma are discharged to ground. Because in many cases of modern day trauma humans are insulated, for example, car accidents, these strong biocurrents are not effectively dissipated. Even if the trauma victim is in contact with the earth, they are often moved to a highly insulated environment of the ambulance, emergency room, hospital bed, etc. It has been determined that these strong bioenergies of trauma are the cause for post traumatic health consequences thereafter. See *Waking the Tiger* by Levine.

SUMMARY OF THE INVENTION

The present invention specifies the fundamental method and system for providing an electrical connection between the human and earth ground for purposes of promoting health, well being, and performance. Because the human bioenergetic system "ramps" energy production up and down as a function of connectedness, the ability to vary the resistance of the connection within a specified range is of import relative to applying the present invention to varying human situations and endeavors including but no limited to healing, rest, exercise, sports competition, mental clarity, sleep, etc.

BRIEF DESCRIPTION OF THE DRAWING FIGS.

The accompanying drawing figures incorporated in and forming a part of this specification illustrate several aspects of the invention and together with the description serve to explain the principles of the invention.

FIG. A presents a high level description of the system of the preferred embodiment of the present invention.

FIG. B presents a table wherein changes in voltage, current, and power are tabulated as a function of changes in resistance between a human and earth ground.

FIG. C presents a graph depicting variations in voltage as a function of variations in resistance between a human and earth ground.

FIG. D presents a graph depicting variations in current as a function of variations in resistance between a human and earth ground.

FIG. E presents a graph depicting variations in power as a function of variations in resistance between a human and earth ground.

FIG. F presents a graph depicting variations in internal impedance as a function of variations in resistance between a human and earth ground.

FIG. G presents a detailed block diagram of the preferred embodiment of the present invention.

FIG. H presents a graph depicting changing biopotential during the therapeutic application of myofascial release, a particular "massage" modality.

FIG. I presents a high level depiction of the grounding kit for use in portable emergency medical applications.

DETAILED DESCRIPTION OF THE PREFERRED EMBODIMENTS

The embodiments set forth below represent the necessary information to enable those skilled in the art to practice the invention and illustrate the best mode of practicing the invention. Upon reading the following description in light of the accompanying drawing figures, those skilled in the art will understand the concepts of the invention and will recognize applications of these concepts not particularly addressed herein. It should be understood that these concepts and applications fall within the scope of the disclosure and the accompanying claims.

The present invention specifies the fundamental method and system for providing a connection between a human and earth ground for purposes of promoting health, well being, and performance. It accomplishes the above stated purpose by:

a) facilitating a viable connection, i.e. transduction of human biopotential, between the human and earth ground,
b) by allowing an individual or clinician to automatically characterize an individual bioenergetic response or signature,
c) by allowing an individual or clinician to specify or program a specific resistance to ground setting for therapeutic or performance purposes,
d) providing programmability of bioenergetic response in all matter of applications. For example, a chair might be programmed for "relaxation" and then switched to "wakeful alertness". This may be accomplished simply by: a) covering it with a conductive fabric, and b) connecting that conductive fabric to earth ground via specific resistive values. The same concept might apply to a pair of shoes, ex. one setting for walking and another for running, and yet another for relaxing,
e) facilitating the application in both fixed and portable medical environments, e.g. hospital rooms vs. emergency medical rescue situations,
f) providing visual indicators indicating both correct operation and program setting.

With the aid of FIGS. A-I, the salient features of the preferred embodiment are now explained in detail. The detailed discussion begins with FIG. A, depicting a high level system diagram of the preferred embodiment of the present invention. The essential system consists of conductive plane (1), conductor (2), variable resistor (3), voltage, current, and power meter (4), ground electrode (5), and human subject (6). Human subject (6) is in contact with conductive plane (1). At an effectively infinite resistance to ground, as measured using a high impedance (1 megohm) volt meter, a typical human biopotential may be in the 20 millivolt range. The human subject my have direct skin-plane contact or may be wearing clothing. Conveniently, the human bioenergy system of interest is capacitively (AC) coupled to the conductive plane so a layer of clothing does not present a problem. This having been said, it is desirable to for the human subject to have as much skin contact as possible, ideally of the torso and head, with the conductive plane. Conductive plane (1) may consist of any highly conductive material, i.e. metal, metalized plastic, carbon impregnated plastic, carbon fiber material, etc. and may take any shape, for example, a bed sheet, a shoe insole, a bicycle seat, etc. With effective coupling of vertebrate biopotential to the conductive plane, alternating current and direct currents flow from the conductive plane to conductor (2), to variable resistor (3), and finally to ground via ground electrode (5). Note that the electrical path just described may be 3 inches long or the length of a building, i.e. it has to do with the application and the accessibility of a low impedance earth ground. As the value of variable resistor (3) increases above zero ohms, voltage across variable resistor (3) increases, this voltage being indicative of current flowing in the circuit. As can be seen in the table of FIG. B, as the value of variable resistor (3) increases up to a certain point, current flowing in the circuit also increases. This is due to a corresponding increase in energy output and a decrease in impedance of the human body in an attempt to maintain maximal current flow to earth ground. Changes in internal impedance as a function of changes in resistance to ground are depicted in the graph of FIG. F. (Current at zero ohms has yet to be measured due to technical challenges.) Power (FIG. E) continues to increase up to a certain point at which the body's energy output will increase no more, nor will the body's internal impedance decrease further. This point is clearly visible as the peak of the power graph (FIG. E) corresponding to a series resistance of 461 ohms between the body and earth ground.

Consequently, the power curve (FIG. E) depicts the functional range of the human biopotential of interest, this range existing between 0 and 10,000 ohms. As previously mentioned, the decreasing impedance of the human body with consequent increasing current, represents a ramping up of available bioenergy, this energy being available for both the purpose of maintaining optimal ground current as well as other functions, for example "work" or "exercise", i.e. activities requiring the supply of bioenergy. Therefore, this patent asserts, that an effective way to increase ones energy for work is to optimally increase the resistance between body and earth, thereby facilitating an increase in available bioenergy. Alternatively, one can decrease ones available energy for purposes of rest, by lowering the resistance, the body's response being to reduce current output and ramp down energy production. As can be seen from the power graph (FIG. E), the body has a relatively linear response above 10 ohms, power increasing at about 0.05 microwatts per 10 ohms up to approximately 500 ohms, at which time body impedance begins to increase as opposed to decrease.

FIG. G presents a more detailed depiction of the functional block diagram of the preferred embodiment of the present invention. Human organism (1) comprises living bioenergy generator (2), variable internal impedance (3), and skin (4) facilitating both AC and DC coupling to conductive plane (5). Again, conductive plane (5) may in practice, may take any shape and may consist of any conductive material to which there is an effective AC and DC coupling with the body. Of course, this flexibility allows for incorporation of the present device into any and all matter of device and applications, for example, furniture, carpet, clothing, exercise gear, automobiles, etc. In preferred embodiments of the present invention, the resistivity of conductive plane (5) will be extremely low. This is required in order to facilitate the full range of programmability between zero ohms and ~10K ohms, as is useful and appropriate for the specific application and time. Generally speaking, the larger the contact area between the subject and conductive plane, the more current will flow and power assessment will be increasingly accurate. For this reason, while a strap or band (as opposed to a larger surface area) can be used, it does not yield the best result.

Variable resistor (6) is in principle a simple manual or automatically variable resistor which may be of the mechanical or electronic variety, i.e. a transistor. In preferred embodiments, the effective resistive value must approximate zero ohms and must be programmable to a maximum value of 10K ohms. It must facilitate the free flow of alternating current and not possess any rectifying properties. For practical diagnostic purposes, it is necessary that variable resistor (6) be "sweepable" such that under control of user interface (7), the "power signature" of a given person (or vertebrate) can be assessed and ultimately analyzed. Power is calculated by user interface, control logic, and power measurement subsystem (7) as a function of voltage drop across variable resistor (6) as measured by voltmeter (8) using the formula:

Power=Voltage$^2$/Resistance

Alternatively power can be assessed by measuring current via a non-obstructive current detector in series with variable resistor (6), for example a Hall effect device. In this case power is computed using the formula:

Power=Current$^2$×Resistance

User interface (7) provides a number of functions including man machine interface, control logic, power calculation, resistor setting, graphical presentation, and visual indicators (9). Minimally visual indicators provide an indication that:
 a) the system is a grounded system and is working properly,
 b) the system is presently programmed for:
  a. zero resistance: <1 ohm to ground
  b. low resistance: <10 ohms to ground
  c. medium resistance: 10-50 ohms
  d. high resistance: 50-500 ohms The present invention can be used to assess medical conditions having to do with health, vitality, age, etc., the height, width, and responsiveness of the curve being indicative of overall bioenergetic robustness. The preferred embodiment of the invention provides the capability to perform a sweep so as to ascertain one's power signature. This signature is presented in graphical form exemplified by FIG. E. The present setting (in use) is then visually highlighted in the context of the power curve. For example, if the resistor setting is set at 461 ohms, the peak of the graph will be illuminated. This allows one to engage in varying activities knowing where they are relative to their own power signature. The percentage of peak power calculated is also visually provided via user interface, control logic, and power measurement subsystem (7) in combination with visual display (9).

Conductor (10) is nonspecific except that it be of a low resistivity. Not unlike the conductive plane, it can take any shape or size and be constructed of any material, again allowing ultimate application flexibility. Generally, this ground conductor should be dedicated to the purpose of grounding bioenergetic current.

While there are numerous potential forms, earth ground is simply a ground rod or other sunken electrode that guarantees a solid and safe earth ground. Generally, this ground electrode should be dedicated to the purpose of grounding bioenergetic current.

Two features exist for the purpose of safety. The first is an "over voltage" function. This function is accomplished by measuring the biopotential of the human subject to ground across 1 M ohm, this being the "open biopotential" at the beginning of application. If at any time, a voltage substantially higher is detected across variable resistor (6), the circuit is opened and remains open until reset. This parameter is programmable. The second safety feature is a fuse that exists at the junction of conductive plane (5) and variable resistor (6). This fuse has a value on the order of 200 microamps and is there to prevent any foreign potentials from finding their way from the ground system, through the circuit of the invention to the human subject.

FIG. H resents a graph depicts changing biopotential during the therapeutic application of myofascial release, a particular "massage" modality that is known to simulate a previous original traumatic event and in doing so, releases "unresolved" bioenergy created during the original traumatic event. As depicted in FIG. H, the biopotential (voltage) doubles during the period of the release. More importantly, the power more than triples from 86 nanowatts to 288 nanowatts. This patent asserts that this increase in power is therapeutic for the human subject as long as the subject is grounded and increased current is allowed to flow between the subject and earth. If this does not occur, this increased biopotential, just as in the original traumatic event, can in itself result in longer term traumatic symptoms. For this reason, it is critically important that a first step in treating trauma victims is to establish an electrical connection between the body of the victim and earth ground.

FIG. I depicts the "grounding kit" for carriage and use during urgent medical care applications requiring grounding portability. It consists of low impedance cable (1), alternative ground electrodes, (2-5), a receptacle verification device (6), at the other end of the cable a low impedance terminal strip (7), the conductive plane (8) which may consist of any conductive material, and low impedance jumpers (9) for connecting terminals to the conductive plane. Clamp electrode (2) is a spring loaded clamp constructed of highly conductive metal that is affixed to an existing ground rod, cold water pipe, or other grounded metallic structure within reach. Spike electrode (3) consists of a foot long nail or similar shaped spike that is driven into the ground at the site of care. Alternatively, if standing water, for example a puddle, is accessible, it can be placed in the water. Flexible mat electrode (4) is used in combination with a liquid conductant, the conductant being applied liberally between the mat and earth, for example on a concrete surface. The flexible mat electrode may also be applied to standing water if available.

Prong electrode (5) is inserted into the verified ground receptacle of a normal AC outlet. This outlet is verified using a standard ground integrity/fault detector verification device (6). Once the electrode is selected depending on the circumstances, it is affixed to the far end of the cable (1) and attached to the ground source. Low impedance jumpers (9) are then connected between terminal strip (7) and conductive plane (8).

Patients undergoing traumatic events in a hospital or clinical setting should be "grounded". Because these are fixed facilities, beds, operating tables, massage tables, etc. can be pre-fitted or manufactured incorporating a preferred embodiment of the present invention and employed both during times of acute stress and trauma as well as during recovery.

Generally speaking, the treatment of trauma requires zero ohms. Other therapeutic, health, well being, and performance objectives employ varying resistances.

Instructive Method for Characterizing the Biopotential of a Human Subject:

This instructive method defines the stepwise method for an individual user or a care practitioner in the characterization of biopotential employing the present invention. For convenience it is written from the prospective of a care practitioner.

1. The care practitioner turns the system "on" enabling measurement and display functions.
2. The care practitioner requests that care recipient to remove as much clothing as is practical. While it is not absolutely necessary, it is highly desirable that there is skin-conductive plane contact with some portion of the torso, the more the better.
3. The care recipient places themselves on the conductive plane, the ideal case being a horizontal surface of body length and width.
4. The care practitioner $1^{st}$ assesses and records the "open biopotential" of the care recipient, in effect the voltage between the conductive plane and ground with no series resistance in place.
5. The care recipient "sweeps" the variable resistor either manually or automatically under control of the user interface and control logic function. Voltage measurements are recorded as resistance varies.
6. The "power curve" is then calculated and presented graphically to both user and health care practitioner.
7. The "open biopotential" and the height, width, and responsiveness of the curve is used to determine general robustness of the care recipient as well as to potentially diagnose certain health issues.
8. The instrument is powered "off" and the care recipient removes themselves from the conductive plane and puts on that clothing that was removed for purposes of assessment.

This concludes the discussion of this instructive method.

Instructive Method for Employing and Applying the "Grounding Kit" for Urgent Medical Care Situations Requiring Grounding Portability:

The objective during emergency medical care is to rapidly establish an electrical connection between the patient and ground. This connection should be as low an impedance as possible to earth ground. The usefulness, if any, of series resistance to ground during times of trauma has yet to be determined.

1. The emergency medical care team arrives, surveys the scene, and rapidly assesses the status of the patient.
2. Depending on the mobility of the patient, the emergency medical care team either treats the patient in place or places the patient on a gurney.
3. If the patient is treated in place, accessible body parts, are wrapped in foil or other conductive fabric, the foil acting as the "conductive plane" of FIG. 1-8.
4. If the patient is moved to a gurney, a sterile foil sheet is applied to the surface of the gurney such that the care recipient is in maximal contact. This foil is the conductive plane of FIG. 1-8.
5. If need be, clothing should be removed so as to establish maximal contact with the foil. Exposed body parts can be wrapped in foil if deemed appropriate.
6. Again depending on the circumstances, an appropriate ground electrode choice is made and applied.
7. The foil is connected via clips and wires to terminals on the electrode cable.
8. At this point the care recipient is grounded.
9. The care recipient should remain grounded for a duration as is determined appropriate by the emergency care practitioner.

This concludes the discussion of this instructive method.

Those skilled in the art will recognize improvements and modifications to the preferred embodiments of the present invention. All such improvements and modifications are considered within the scope of the concepts disclosed herein and the claims that follow.

What is claimed:

1. A method for identifying energy output from a vertebrate organism connected to ground for the purpose of promoting health, well being, and performance, comprising the steps of:
   electrically connecting a vertebrate organism to a ground;
   varying current flow between the vertebrate organism and the ground by varying a series resistance between the vertebrate organism and the ground over a resistance range; and
   determining an energy output from the vertebrate organism to the ground over the variation in the series resistance as a function of the series resistance.

2. The method of claim 1, further comprising measuring a voltage across the series resistance,
   wherein the determining an energy output comprises determining an energy output from the vertebrate organism to the ground over the variation in the series resistance as a function of the measured voltage squared divided by the series resistance.

3. The method of claim 1, further comprising measuring a current flowing through the series resistance,
   wherein the determining an energy output comprises determining an energy output from the vertebrate organism to the ground over the variation in the series resistance as a function of the measured current flowing through the series resistance squared times the series resistance.

4. The method of claim 3, wherein the measuring the current flowing through the series resistance comprises non-obstructively measuring the current flowing through the series resistance.

5. The method of claim 1, further comprising determining from the energy output at which series resistance the energy output from the vertebrate organism is at a maximum energy output.

6. The method of claim 5, further comprising measuring a voltage across the series resistance,
   wherein the determining at which series resistance the energy output from the vertebrate organism is at a maximum energy output comprises determining at which series resistance the energy output from the vertebrate organism is at the maximum energy output as a function of the measured voltage squared divided by the series resistance.

7. The method of claim 5, further comprising measuring a current flowing through the series resistance,
   wherein the determining at which series resistance the energy output from the vertebrate organism is at a maximum energy output comprises determining at which series resistance the energy output from the vertebrate organism is at the maximum energy output as a function of the measured current flowing through the series resistance squared times the series resistance.

8. The method of claim 1, wherein the resistance range comprises approximately 0 ohms to approximately 10,000 ohms.

9. The method of claim 1, wherein the ground is earth.

10. The method of claim 1, wherein the electrically connecting a vertebrate organism to a ground comprises connecting the vertebrate organism to a conductive plane which is coupled to a ground via the series resistance.

11. The method of claim 1, further comprising programming a variation of the series resistance, wherein the varying a series resistance between the vertebrate organism and the ground over a resistance range comprises varying a series resistance between the vertebrate organism and the ground over the programmed variation of the series resistance.

12. The method of claim 1, further comprising displaying the energy output on a display.

13. The method of claim 12, wherein displaying the energy output on a display comprises displaying present energy output on the display in a percentage of peak energy output relative to a power signature of the vertebrate organism.

14. The method of claim 1, wherein the vertebrate organism is a human.

15. A device for identifying energy output from a vertebrate organism connected to ground for the purpose of promoting health, well being, and performance, comprising:
 a variable resistor for providing a series resistance between a vertebrate organism and a ground for varying current flow between the vertebrate organism and the ground over a resistance range; and
 a detector for determining an energy output from the vertebrate organism to the ground over the resistance range as a function of the series resistance.

16. The device of claim 15, further comprising an electrical connector to connect the vertebrate organism to the ground.

17. The device of claim 16, wherein the electrical connector is provided as part of a system throughout a building for purposes of grounding one or more facilities in the building.

18. The device of claim 15, further comprising a display adapted to display the energy output.

19. The device of claim 18, wherein the display further comprises visual indicators to indicate the series resistance and that the vertebrate organism is connected to the ground.

20. The device of claim 16, wherein the electrical connector is part of a grounding kit further comprising one or more of the following devices: a low impedance cable, one or more electrodes, a ground integrity/fault detection device, a terminal strip, one or more low impedance jumpers, and one or more conductive plane materials.

21. The device of claim 15, wherein the detector determines the energy output over the resistance range, by measuring a voltage across the series resistance, and dividing the measured voltage squared by the series resistance.

22. The device of claim 15, wherein the detector determines the energy output by, over the resistance range, measuring a current flowing through the series resistance, and multiplying the measured current squared by the series resistance.

23. The device of claim 22, wherein the detector further comprises a non-obstructive current measuring device to measure the current flowing through the series resistance.

24. The device of claim 15, wherein the detector is further adapted to determine a maximum energy output from the vertebrate organism from the detected energy output.

25. The device of claim 15, wherein the vertebrate organism is a human.

* * * * *